United States Patent [19]
Girotti et al.

[11] Patent Number: 5,811,612
[45] Date of Patent: Sep. 22, 1998

[54] CATALYTIC COMPOSITION AND PROCESS FOR THE ALKYLATION OR TRANSALKYLATION OF AROMATIC COMPOUNDS

[75] Inventors: Gianni Girotti, Bologna; Oscar Cappellazzo, Alghero, both of Italy

[73] Assignee: Enichem Synthesis S.p.A., Palermo, Italy

[21] Appl. No.: 478,831

[22] Filed: Jun. 7, 1995

[30] Foreign Application Priority Data

Jun. 15, 1994 [IT] Italy .................................. MI94A1252

[51] Int. Cl.$^6$ ...................................................... C07C 2/68
[52] U.S. Cl. ............................ 585/467; 585/475; 502/63; 502/64
[58] Field of Search ........................ 502/64, 63; 585/467, 585/475

[56] References Cited

U.S. PATENT DOCUMENTS

| | | | |
|---|---|---|---|
| 4,968,405 | 11/1990 | Wachter | 208/120 |
| 5,118,896 | 6/1992 | Steigelmann et al. | 585/467 |
| 5,166,111 | 11/1992 | Zones et al. | 502/64 |
| 5,182,242 | 1/1993 | Marler | 502/66 |
| 5,221,648 | 6/1993 | Wachter | 502/68 |
| 5,587,137 | 12/1996 | Swaroop et al. | 423/239.2 |

Primary Examiner—Gary P. Straub
Assistant Examiner—Thomas G. Dunn, Jr.
Attorney, Agent, or Firm—Oblon, Spivak, McClelland, Maier & Neustadt, P.C.

[57] ABSTRACT

A catalytic composition is described for the alkylation or transalkylation of aromatic compounds consisting of zeolite Beta, as such or modified by the isomorphic substitution of aluminium with boron, iron or gallium or by the introduction of alkaline/earth-alkaline metals following ion exchange processes, and of an inorganic ligand, wherein the extrazeolite porosity, i.e. the porosity obtained by adding the mesoporosity and macroporosity fractions present in the catalytic composition itself, is such as to be composed for a fraction of at least 25% of pores with a radius higher than 100 Å.

16 Claims, 7 Drawing Sheets

CATALYTIC COMPOSITION AND PROCESS FOR THE ALKYLATION OR TRANSALKYLATION OF AROMATIC COMPOUNDS

BACKGROUND OF THE INVENTION

1. Field of the Invention

The present invention relates to catalytic compositions consisting of zeolite Beta (as such or modified) and a ligand which can be used particularly in processes for the alkylation of aromatic hydrocarbons with olefins, in particular benzene with light olefins and more specifically with ethylene to give ethylbenzene and with propylene to give cumene. The catalytic composition of the present invention is also particularly suitable in the transalkylation of aromatic hydrocarbons with polyalkylated aromatic hydrocarbons, especially of benzene with diethylbenzene to give ethylbenzene and benzene with diisopropylbenzene to give cumene.

2. Description of the Background

Former alkylation processes, still widely used in the petrolchemical industry for the production of the two organic intermediates quoted above, involve the use of a catalyst based on phosphoric acid and infusorial earth in a fixed bed for cumene and $AlCl_3$ in slurry for ethylbenzene. The possibility of substituting these catalysts with non-polluting, non-corrosive and regenerable materials such a zeolitic catalysts has been known for some time.

There are mainly two types of problems however arising from the use of zeolitic catalysts in alkylation reactions such as those listed above:

a higher percentage of polyalkylated by-products;

a more rapid deactivation of the zeolitic catalyst.

The first problem compels the use of a second reactor, if the alkylation step is carried out at an insufficiently high temperature, for recovering said by-products, mainly consisting of dialkylates, by transalkylation with benzene, or their direct recycling into alkylation if instead this step is carried out at a sufficiently high temperature.

On the other hand, the second problem, a more rapid deactivation of the catalyst, compels a certain frequency of necessary thermal regenerations which will be greater in number the shorter the duration of the single reaction cycle intended as the duration of the catalyst between two successive thermal regenerations. It is in fact evident that a greater duration of the single reaction cycle will lead to a lower total number of thermal regenerations, with the same complete duration of the catalyst, and on the other hand this complete duration may in turn depend on the total number of thermal regenerations undergone by the catalyst itself and can therefore increase with a greater duration of the single reaction cycle.

The increase in duration per single reaction cycle and consequently in the productivity can be basically obtained by proceeding in two directions:

by non-thermal regeneration techniques in situ as to allow for minimum shiftings or which may easily be accomplished with respect to normal running conditions in the reaction;

intervening on the catalyst.

Various patents claim processes and expedients in the first direction indicated; for example patent PCT/92/02877 describes a process for extending the duration of the single reaction cycle between two thermal regenerations for catalysts based on zeolites in alkylation reactions; this process basically consists in the continuous feeding of a moderate concentration of $H_2O$ together with the reagents.

U.S. Pat. No. 5,518,897 discloses instead a process for reactivating catalysts based on zeolites in alkylation reactions by interruption of the olefin stream and substitution with a moderate stream of hydrogen under certain conditions and for a certain period of time. This would enable the catalytic activity to be brought back to normal values and thus lengthen the duration of the single reaction cycle before thermal regeneration. As far as the second point is concerned, i.e. the preparation of a catalyst with particular duration characteristics per single reaction cycle, it is possible to cite for example U.S. Pat. No. 4,870,222 which claims an alkylation and transalkylation process for producing cumene with the use of an amorphous silica/alumina catalyst in alkylation and a second catalyst based on mordant in transalkylation.

The catalyst based on mordant bound with alumina used in transalkylation is subjected to a modification treatment of the porous structure in order to obtain a higher Specific Surface Area value (SSA) equal to at least 580 $m^2/g$.

It is evident that the value is typical of the components zeolite mordant and alumina, used in the preparation of the catalyst and also obviously depends on the relative percentage actually present; the patent cites an example relating to a material containing 10% of ligand and which after the treatment claimed increases the SSA from 540 $m^2/g$ to 620 $m^2/g$. This treatment creates a greater activity of the catalyst in transalkylation and also a longer duration as shown by the life tests described in the examples of the patent.

SUMMARY OF THE INVENTION

We have found that in the case of catalysts prepared starting from zeolite Beta and an inorganic ligand, used in alkylation reactions of aromatics with light olefins, there is a surprising effect of the porous structure of the catalyst, rather than its SSA, in particular of the porous structure not related to the microporosity itself of the Beta zeolite and more specifically of the Pore Size Distribution of the meso- and macro-porous fractions present in the catalyst. The catalysts we have found have certain porosity characteristics which guarantee high performances in terms of duration and therefore productivity for each reaction cycle, together with excellent mechanical characteristics such as crushing strength and abrasion resistance.

DETAILED DESCRIPTION OF THE INVENTION

Figure 1:
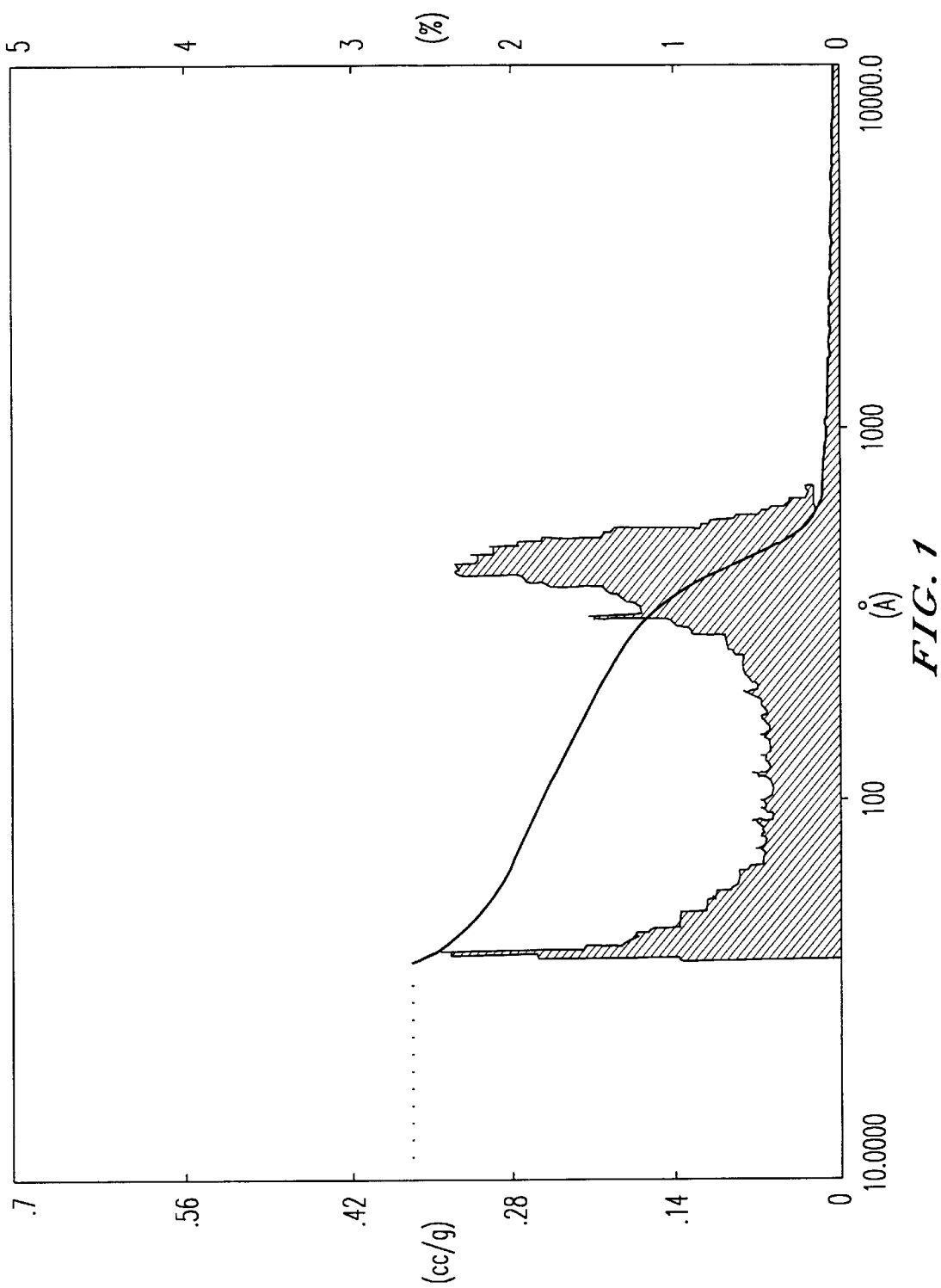
FIGS. 1–4 are graphs showing pore size distribution for Catalysts A–D, in Examples 1–4, respectively.

The catalytic composition of the present invention by the alkylation of aromatic compounds, consists of:

zeolite Beta, as such or modified by the isomorphic substitution of aluminium with boron, iron or gallium or modified by the introduction of alkaline and/or earth-alkaline metals following ion-exchange processes;

an inorganic ligand preferably selected from silicon, aluminium, zirconium, magnesium oxides or natural clays or combinations of these,
and is characterized in that the extrazeolite porosity, i.e. the porosity obtained by adding the mesoporosity and macroporosity fractions present in the catalytic composition itself, (consequently excluding the contribution of microporosity relating to the zeolite Beta), is such as to consist for a fraction of at least 25%, preferably at least 35%, of pores with a radius higher than 100 Å.

The productivity and therefore duration per single reaction cycle is infact more than double if the catalyst possesses this particular porosity which is the main characteristic of the present invention and this effect is independent from the type of inorganic ligand used. The porosity in the fraction with a radius which is greater than 450 Å should preferably be less than 0.25 cc/g when the diameter of the catalytic particles is less than or equal to 0.8 mm. The role of the porous structure claimed herein is evidently intended to reduce the deactivation rate of the catalyst i.e. the rate of deposition of the carbonious products formed during the reaction, responsible for the deactivation.

It is clear from the following examples that there is probably a problem relating to the diffusion of the reagents and products, a so-called morphological diffusion, through the porous structure of the catalyst in the part non related to the zeolite, i.e. through the meso- and macro-porosity fraction; in spite of the greater width of the pores this fraction is in fact characterized by a lesser connectivity and greater twisting with respect to the tridimensional, neat and open-ended channels typical of the zeolite Beta which form the microporosity present in the catalyst and inside which the catalytic activity takes place.

This catalyst therefore has certain porosity characteristics which guarantee high performance in terms of duration and consequently productivity per single reaction cycle, together with excellent mechanical characteristics such as crushing strength and abrasion resistance.

Zeolite Beta, made known through U.S. Pat. No. 3,308,069, is a synthetic, crystalline, porous material having the composition

wherein x is less than 1, y is between 5 and 100, w between 0 and 4, M is a metal of the groups IA, IIA, IIIA or a transition metal and TEA is tetraethylammonium.

The zeolite Beta used can be in any form (acid, partially acid or containing alkaline and/or earth-alkaline cations).

Modifications of zeolite Beta can be obtained by the partial or total isomorphous substitution of aluminium with boron: patent BE-877205 for example describes a porous crystalline boron-silicate called boralite-B, patent application EP-55046 describes an isomorphous zeolite with zeolite Beta in which the aluminium has been partially substituted with boron, iron or gallium; patent application IT-M193A001295 describes a modification by ionic exchange to introduce controlled quantities of alkaline and/or earth-alkaline metals.

Zeolites Beta modified by the introduction of suitable quantities of alkaline and/or earth-alkaline ions are prepared as described in U.S. Pat. No. 3,308,069, subsequent exchange with ammonium and calcination to obtain the zeolite Beta in a completely acid form, further exchange to introduce calibrated quantities of an ion selected from $Na^+$, $K^+$ or $Ca^{2+}$. The exchange is carried out using the known techniques, as described by R. P. Townsend in "Ion exchange in zeolites", Studies Surf.Scien.Cat., vol. 58, pages 359–390, 1991. The sodium, potassium and calcium salts which can be used for the exchange are for example the corresponding acetates, nitrates and chlorides.

The catalyst is prepared starting from zeolite Beta and an inorganic ligand by a process capable of creating a porosity which can be determined "a priori" and in accordance with the present invention.

The catalyst prepared starting from the above components has in fact a rather extended porosity which can be basically defined as trimodal for the contemporaneous presence of microporosity, mesoporosity and macroporosity defined according to the Dubinin classification indicated in Surface Area Determination-IUPAC-Proceedings of the International Symposium on Surface Area Determination, Bristol U.K. 1969.

In particular the ranges of porosity which we refer to are the following:

| | |
|---|---|
| ∞ > radius pores Å > 1000 | macroporosity |
| 1000 > radius pores Å > 15 | mesoporosity |
| 15 > radius pores A | microporosity |

The porosity of the catalyst depends in fact on both the components, which have only microporosity as far as zeolite Beta is concerned and generally mesoporosity as far as the inorganic ligand is concerned, and on the particular process used for producing the catalyst, necessary for its use in, for example, fixed-bed reactors.

The production process used by us has absolutely no influence on the microporosity present in the catalyst, which obviously only depends on the percentage of zeolite Beta present, but rather on the quantity of mesoporosity and macroporosity, i.e. on the so-called extrazeolite fraction of porosity present in the catalyst.

The porosity of the catalyst is measured using two different techniques such as physical absorption of nitrogen at liquid nitrogen temperature with a Carlo Erba Sorptomatic 1990 instrument, and the intrusion of mercury under pressure with a Carlo Erba Porosimeter 2000 instrument, basically following the indications contained in chapters 12 and 13 and chapter 20 of the volume Introduction to Powder Surface Area—Lowell, Seymour-Wiley Interscience publ. with respect to the analysis conditions.

The process used for forming the catalyst of the present invention can be of any kind: the catalyst can in fact be prepared in the form of pellets, bars, cylinders or any other form considered suitable for its use in alkylation reactions of aromatics with light olefins and in particular with ethylene and propylene. The extrusion process is preferably used, i.e. the production of the catalyst into small cylinders called pellets.

The parameters actually used during the preparation of the catalyst into pellets are essential for controlling and obtaining the porosity characteristics indicated above.

This control depends on several factors of which the most important are undoubtedly the extrusion back-pressure and particle size of the zeolite Beta and inorganic ligand used.

With the same components the control of the extrusion back-pressure can therefore be carried out by the modification of different variables typical of an extrusion process including the type of machine used, the revolution speed of the compressing section, the diameter of the output holes or nozzles of the extruded fresh product, the feeding humidity of the extruder, the quantity and quality of the peptizing agent possibly used for the preparation of the feeding to the extruder and the presence of particular substances suitable for giving plasticity and flowability characteristics during extrusion.

What remains important however is the definite possibility of precisely determining the porous structure of the catalyst within the extrazeolite range of porosity, i.e. which can not be attributed to the quantity and quality of the percentage of zeolite present in the catalyst, by controlling the above variables.

Experts in production processes of catalysts and in particular experts in extrusion certainly know the effect, contribution and role of the above variables in determining the porous structure of a catalyst prepared in this way and can therefore reproduce without difficulties the characteristics of the catalytic composition claimed herein.

The catalytic composition of the present invention is particularly suitable in alkylation processes of aromatics with light olefins and particularly benzene with ethylene to give ethylbenzene and with propylene to give cumene.

The alkylation reaction can be industrially carried out on a continuous, semi-continuous and batch scale, and in a gas, liquid or mixed phase; the catalyst can be contained in one or more catalyst beds inside the reactor and the system can contain several reactors in series.

The feeding of the olefin can be more or less distributed along the reactor or between several catalyst beds in order to minimize the polyalkylation reactions of the aromatic substrate and in such quantities as to have a molar ratio [Aromatic]/[Olefin] preferably of between 1 and 20, even more preferably between 2 and 8. The reaction temperature is between 100° C. and 300° C., preferably between 120° C. and 230° C.; the pressure is between 10 atm and 50 atm, preferably between 20 atm and 45 atm; the WHSV space velocity is between 0.1 and 200 $h^{-1}$, preferably between 1 and 10 $h^{-1}$.

It should be noted however that the combination of temperature and pressure conditions actually used must be such as to guarantee that the alkylation reaction basically takes place in the liquid phase.

Using the catalytic composition of the present invention in alkylation processes, a longer life and productivity of the catalyst can be obtained per single reaction cycle with respect to the materials prepared not according to the present invention.

This result is undoubtedly due to the particular pore distribution which is the fundamental characteristic of the catalyst of the present invention.

More specifically, as can be clearly seen in the examples below, the variation of parameters relating to the porous structure in the catalysts of the present invention compared to materials not in accordance with this, after an accelerated catalytic test with partial deactivation of the catalyst, is in fact qualitatively and quantitatively different.

This variation can naturally be clearly observed from the direct measurement of the fractions of micro-, meso- and macro-porosity in the catalysts after the catalytic test. The variations can be even more clearly noted after determining the SSA parameter (Specific Surface Area) in the fresh and deactivated catalysts. The determination of the SSA on fresh catalysts and following the catalytic test, described in the examples below, is carried out by physical nitrogen adsorption as described above and processing the experimental isotherm data obtained according to the BET theory.

The BET theory is an extension of the Langmuir theory for multistrate physical adsorption and can be successfully applied in the interpolation of adsorption isotherms of the type I, II and IV (according to the Brunauer, Deming and Teller classification) as indicated by S. Brunauer, P. H. Emmet and E. Teller, J.Amer.Soc., 60,309(1938) and in S. J. Gregg, K. S. W. Sing, Adsorption, Surface Area and Porosity, Academic Press London 2nd ed.(1982).

The catalytic compositions of the present invention and generally all materials containing not a low percentage of component having microporosity generate a physical adsorption isotherm with type I characteristics (typical of microporous materials) however associated with type IV isotherm characteristics (typical of mesoporous materials) if there is a mesoporosity component.

In this case the SSA determination using the BET theory compels the use of the particular form of the so-called 3 parameter equation, i.e. not linear (H. Reichert, Diplomarbeit, Joh.Gutenberg Universitat, Mainz 1988). The interpolation of the physical adsorption experimental isotherm provides Vm (monolayer volume) values, necessary for calculating the SSA, C(BET) and N(M. Avriel, Nonlinear Programming, Prentice Hall, 224 (1976).

As a consequence of the physical meaning which the BET theory assigns to the C(BET) and N parameters it can be observed that the C(BET) parameter decreases as the microporosity character decreases whereas the N parameter increases and these parameters can therefore be considered as indexes of the content or residual character of microporosity of the materials being examined.

In all the materials prepared it can in fact be noted that the variation of the above parameters is in the sense indicated by the catalytic test and deactivation, considering that microporosity is the fraction of porosity of the catalyst inside which the catalytic activity mainly takes place, these parameters are particularly useful for following the observed variation due by the same microporous fraction in the catalyst after the catalytic test.

The direct measuring of the fraction of microporosity as specified above is carried out by physical nitrogen adsorption and by the t-plot made according to de Boer (B. C. Lippens and J. H. de Boer, J.Catalysis, 4,319, 1965).

The catalytic compositions of the present invention have in fact a different variation of these parameters and micorporosity content after deactivation compared to those not in accordance with the present invention. In practice analysis of the porous structure of the deactivated materials after the catalytic tests described in the following examples shows that the greater productivity and longer life in alkylation reactions with olefins are accompanied by a greater loss of microporosity, i.e. of the porosity responsible for the catalytic activity, in the catalytic compositions claimed herein.

The materials which are not in accordance with the present invention and therefore having a lower productivity and shorter life, show, after deactivation, an even higher microporosity content which is evidently however no longer accessible for obtaining the catalytic activity.

In practice the presence of a fraction of porosity which is higher than 100 Å in radius, equal to at least 25% of the extrazeolite porosity in the fresh catalyst, guarantees a lower deactivation rate owing to a greater use of the microporous fraction of the catalyst, i.e. of the fraction responsible for the catalytic activity during alkylation reactions of benzene with olefins.

The catalytic composition of the present invention is also particularly suitable in the transalkylation processes of aromatic hydrocarbons with polyalkylated aromatic hydrocarbons. The aromatic hydrocarbon can be selected from benzene, toluene, ethylbenzene and xylene and preferably benzene.

The polyalkylated aromatic hydrocarbon is preferably selected from diethylbenzene and diisopropylbenzene. The transalkylation of benzene with diethylbenzene to give ethylbenzene and benzene with diisopropylbenzene to give cumene are particularly preferred.

The transalkylation reaction must be carried out under such conditions as to take place at least partially in the liquid phase. It is preferably carried out at a temperature of between 100° and 350° C., at a pressure of between 10 and 50 atms and at a WHSV of between 0.1 and 200 hours$^{-1}$. Even more preferably, the temperature is between 150° C. and 300° C., the pressure is between 20 and 45 atms and the WHSV is between 0.1 and 10 hours$^{-1}$. The molar ratio between aromatic hydrocarbon and polyalkylated aromatic hydrocarbon can vary between 1 and 30.

According to a preferred aspect of the present invention the polyalkylated aromatic hydrocarbon prevalently or totally consists of diisopropylbenzene or prevalently or totally consists of diethylbenzene. For example the fraction "cumene bottoms" produced in akylation processes to give cumene can be used as polyalkylated aromatic hydrocarbon prevalently consisting of diisopropylbenzene.

The following examples provide a better illustration of the present invention but do not limit it in any way.

EXAMPLES

Preparation of the Zeolite Beta Used in the Examples 58.8 g of tetraammonium hydroxide at 40% by weight in an aqueous solution and 1.9 g of sodium aluminate are added to 58.4 g of demineralized water. The mixture is heated to about 80° C. and is left under stirring until complete dissolution. The limpid solution thus obtained is added to 37.5 g of Ludox HS colloidal silica at 40% by weight. A homogeneous suspension is obtained having pH 14, which is charged into a steel autoclave and left to crystallize under hydrothermal conditions at 150° C. for 10 days, under static conditions and at autogenous pressure. The crystallized product is separated by filtration, washed, dried for 1 hour at 120° C., calcined for 5 hours at 550° C. and ion-exchanged into acid form by treatment with ammonium acetate and subsequent calcination.

The sample thus obtained, upon chemical analysis, has the following composition expressed as a molar ratio:

$SiO_2/Al_2O_3 = 19.3$

The product was characterized by power X-ray diffraction.

Example 1

A catalyst called CATALYST A is prepared, based on zeolite Beta (whose preparation is described above) and alumina following an extrusion process whose main parameters effectively used are indicated in Table I together with the relative porosity values of the end catalyst.

The extrusion parameters indicated in Table I guarantee the production of a material with the particular Pore Size Distribution claimed herein and shown in FIG. 1 for the catalyst prepared as described above (FIG. 1 also indicates in ordinate the cumulative volume in cc/g and the percentage (%) of said volume and in abscissa the pore radius in Å).

As can be seen from FIG. 1 there are basically two fractions present within the porosity indicated by the porosimeter (>37 Å) and i.e. the fraction up to 100 Å of radius and the higher one; the second is in fact predominant and falls into the particular Pore Size Distribution claimed.

Example 2—Comparative

A catalyst called CATALYST B is prepared using the same components as example 1 but substantially modifying the extrusion process and using the parameters described in Table II which also indicates the data concerning the porosity of the end catalyst.

Figure 2:
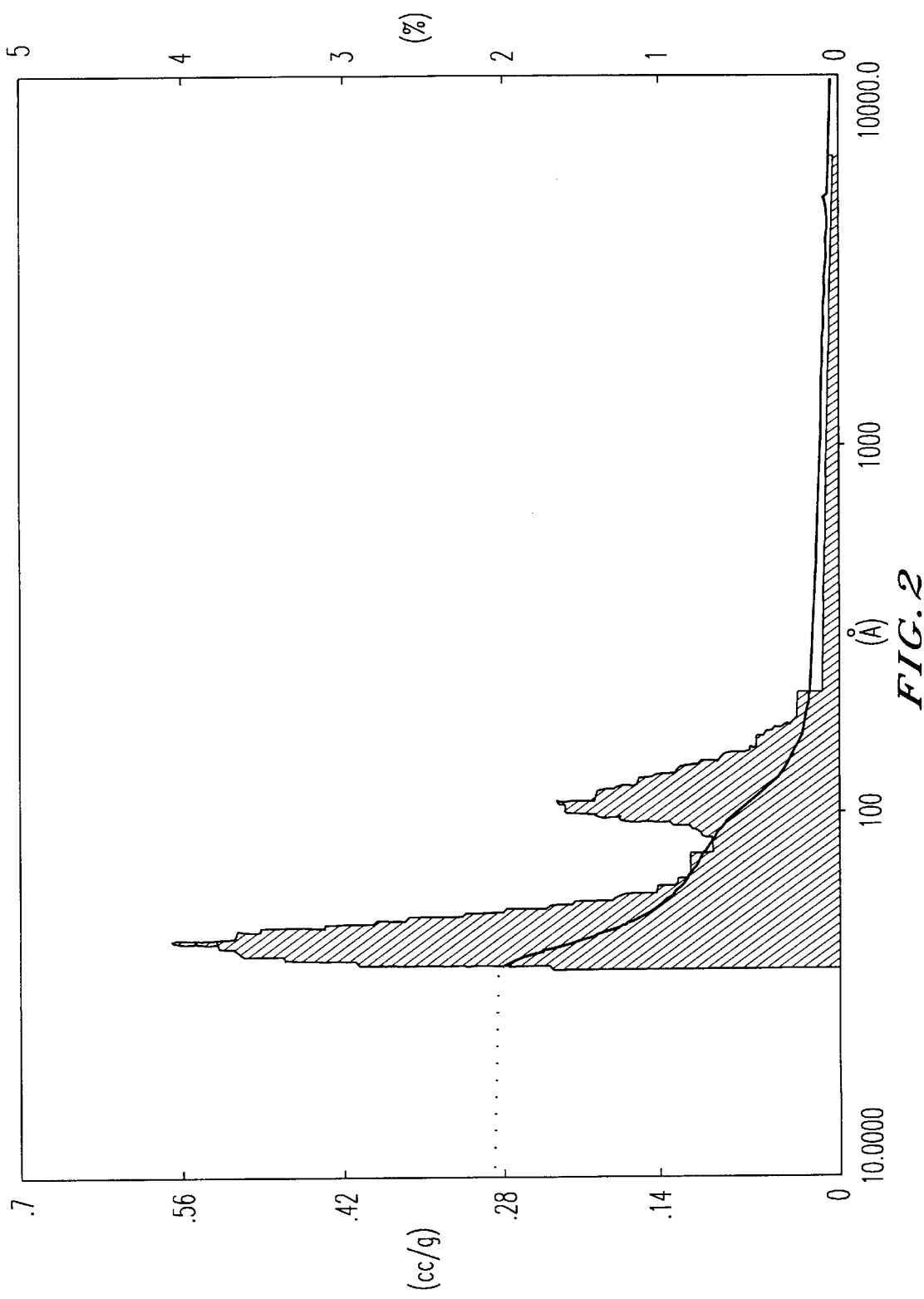

FIG. 2 shows the Pore Size Distribution obtained from the porosimeter from which it can be noted that the greater part of extrazeolite porosity consists of pores with a radius of less than 100 Å.

Example 3

A catalyst called CATALYST C is prepared using the same components as example 1 but substantially modifying the extrusion process and using the parameters described in Table III which also indicates the data concerning the porosity of the end catalyst.

Figure 3:
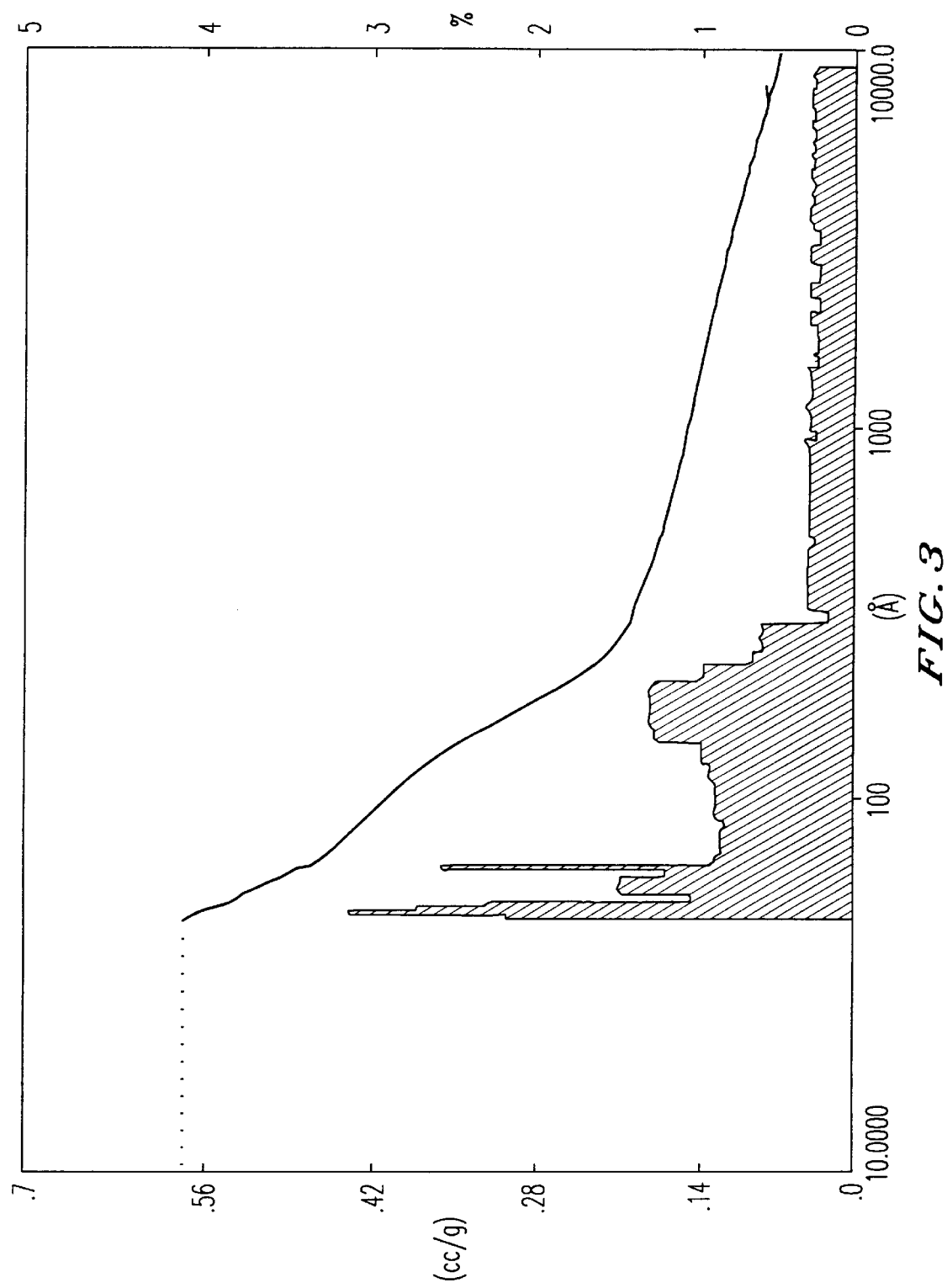

FIG. 3 shows the Pore Size Distribution obtained from the porosimeter from which it can be noted that the greater part of extrazeolite porosity consists of pores with a radius higher than 100 Å.

Example 4

Figure 4:
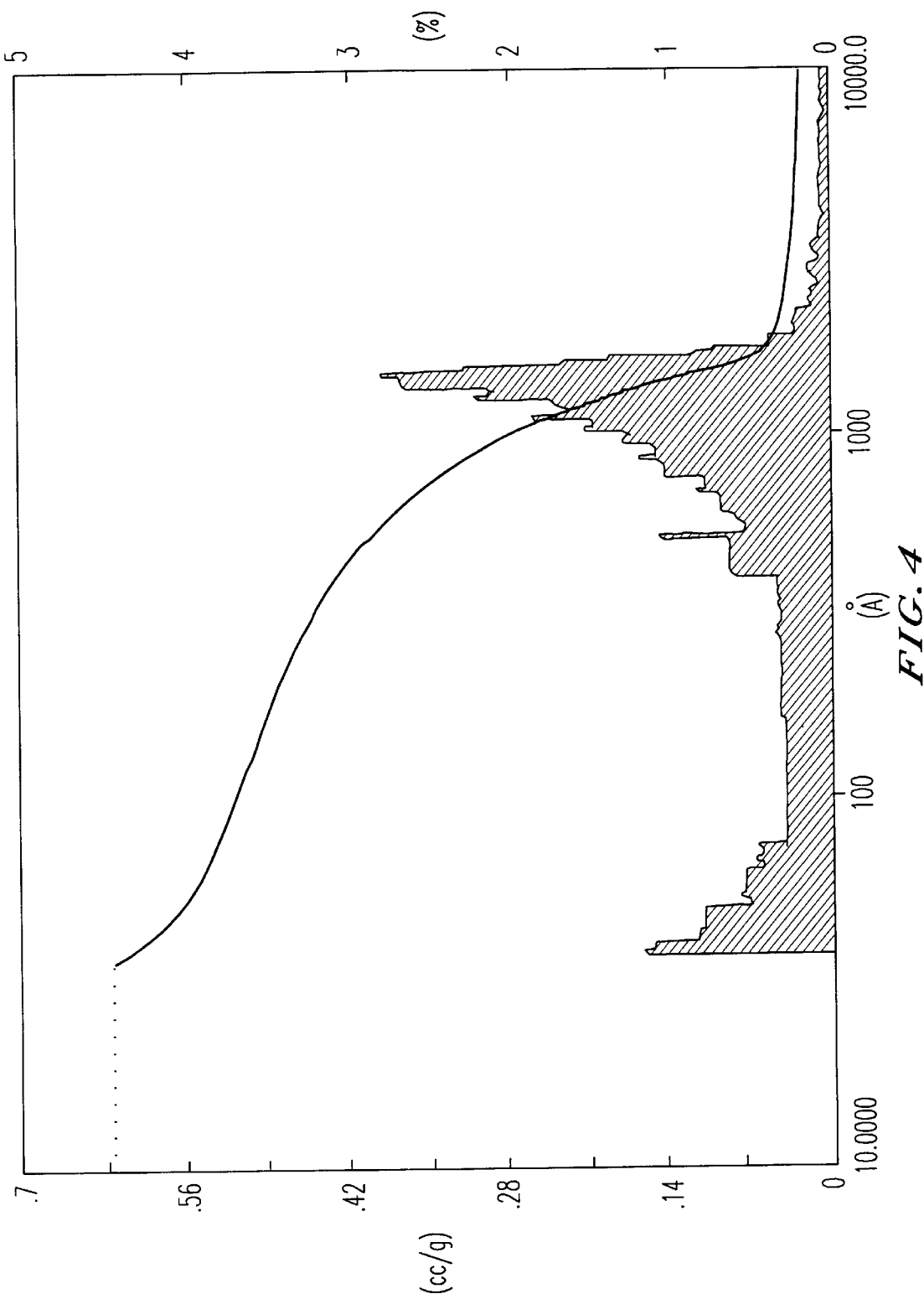

A catalyst called CATALYST D is prepared substantially modifying the extrusion process as indicated in table IV and using silica/alumina as inorganic ligand. FIG. 4 shows the Pore Size Distribution obtained from the porosimeter from which it can be noted that the greater part of extrazeolite porosity consists of pores with a radius higher than 100 Å.

Example 5

An alkylation test of benzene with propylene is carried out using an experimental device consisting of a micropilot catalyst fixed-bed reactor made of Inconel 600 with an internal diameter of 2 cm and total length of 80 cm, feeding tanks for benzene and propylene, dosage pumps for the separate feeding of the two reagents in the liquid phase, temperature and pressure control, automatic discharge of the effluent from the reactor and automatic sampling system of the feeding and effluent from the reactor for continuous analysis of the reagents and products.

This analysis is carried out with an HP 5890 gas-chromatograph connected to a processor, carrier gas He, steel column of ⅛"×1.5 mt packed with FFAP 15% on Chromosorb W-AW, injector temperature 250° C., Temperature programmed from 50° to 220° C., detector temperature 250° C. and TCD detector for feeding to the reactor.

The reactor effluent is analyzed with a DANI 8520 gas-chromatograph connected to a processor, carrier gas He, capillary column in molten silica with an internal diameter of 0.2 mm length of 50 mt and eluating liquid methylsilicon 0.5 micron, injector temperature 250° C., temperature programmed from 40° to 240° C., detector temperature 250° C. and FID detector.

The reaction conditions used during the test are the following:

Inlet T=150° C.
P=30 bar
WHSV=5.5 hr$^{-1}$
[Benzene]/[Propylene]=5.7

4.5 g of catalyst prepared as described in example 1 (CATALYST A) and 11.5 of inert material are then charged.

Figure 5:
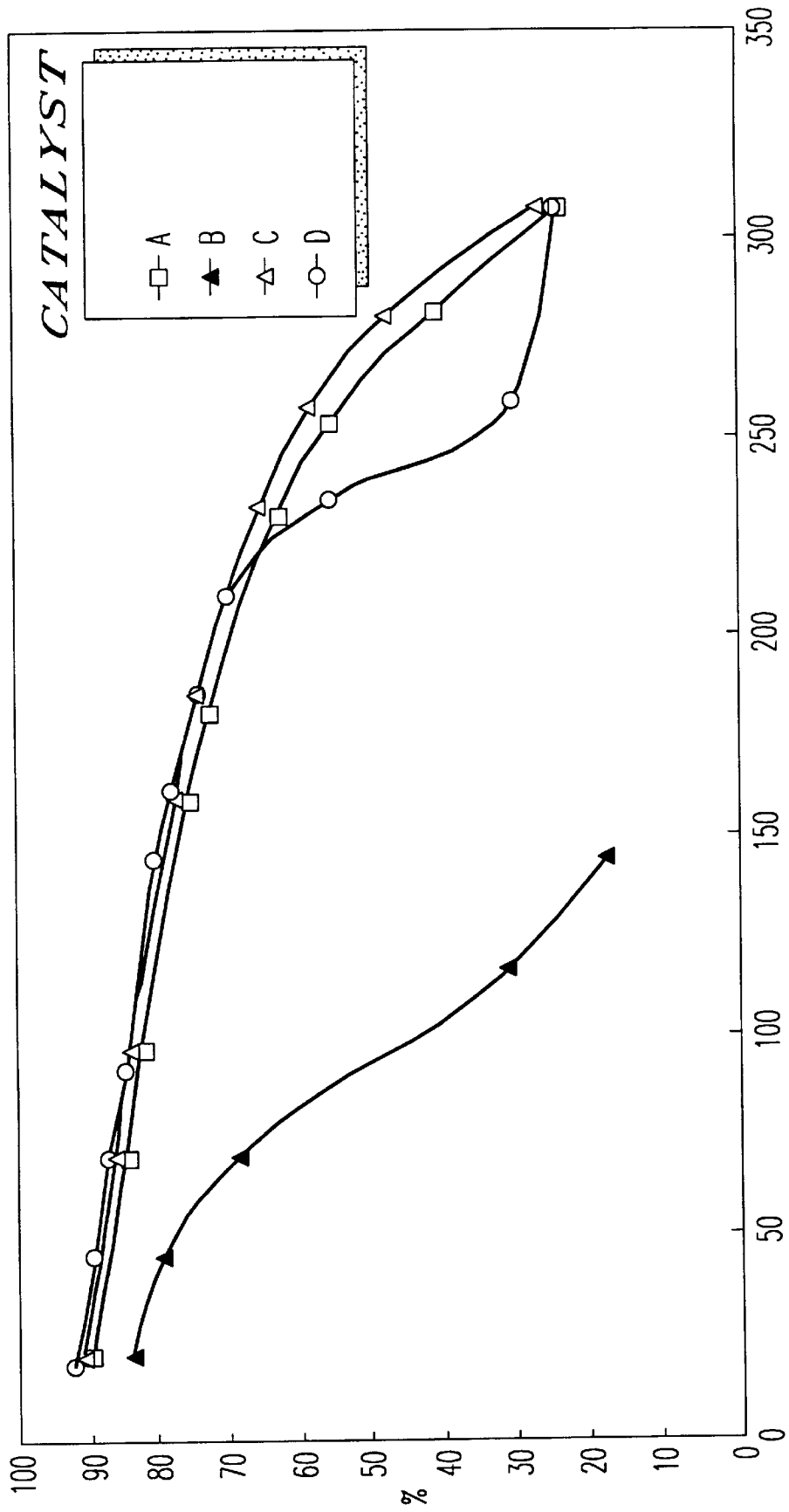
FIG. 5 is a graph showing the conversion trend of propylene in relation to the time on stream for each of Catalysts A–D, in Examples 5–8, respectively.

FIG. 5 shows the conversion trend of propylene in the ordinate (%) in relation to the "time on stream" in hours (hr) in the abscissa obtained using a bench reactor.

As can be seen from FIG. 5 the conversion of propylene at the end of the test was equal to about 27% after 307 continuous running hours without any modification of the above reaction conditions.

Table V shows the data relating to the porosity of the catalyst at the end of said test.

As can be noted from comparing the values of table V with those indicated for the fresh catalyst in table I, there has been a total drop in porosity mainly on the part of the microporous fraction.

This can also be observed from parameters "C" and "N" obtained by BET processing whose variation is a definite indication of the decrease in the microporosity.

Example 6—Comparative

The catalyst prepared as described in example 2 (CATALYST B) is charged under the same conditions as example 5.

The conversion trend of the propylene during the test in relation to the time on stream is shown in FIG. 5. As can be seen in FIG. 5 the conversion of propylene at the end of the test was equal to about 19% after only 144 continuous running hours without any modification of the above reaction conditions.

Table VI shows the data relating to the porosity of the catalyst at the end of this test.

As can be seen from comparing the values of table VI with those indicated for the fresh catalyst in table II, there has been a total drop in porosity mainly on the part of the mesoporous fraction i.e. the fraction of porosity other than the micropores present in the catalyst.

Unlike the results obtained in the previous example it can be observed that also when the productivity is less than half with respect to the previous example the microporous fraction where the catalytic activity occurs is still mainly free but evidently not accessible to the reagents as can be seen from observing the data shown in FIG. 5.

On the other hand the conservation of a greater microporosity, with respect to the previous example for this material after the catalytic test, is perfectly clear from observing parameters "C" and "N" whose variation is in fact considerably different and to a lesser extent compared with the material of the previous example.

It is therefore evident that this catalyst, which is not in accordance with the present invention, is characterized by a greater deactivation rate with respect to the material relating to the present invention and prepared as described in example 1.

Example 7

The catalyst prepared as described in example 3 (CATALYST C) is charged under the same conditions as example 5.

The conversion trend of the propylene during the test in relation to the time on stream is shown in FIG. 5. As can be seen from FIG. 5 the conversion of propylene at the end of the test was equal to about 30% after 300 hours of continuous running without any modification of the above reaction conditions.

It is clear that the performances of the catalyst can be perfectly compared, with respect to the life and consequently productivity of the catalyst, with those obtained using the material prepared according to example 1.

Example 8

The catalyst prepared as described in example 4 (CATALYST D) is charged under the same conditions as example 5.

The conversion trend of the propylene during the test in relation to the time on stream is shown in FIG. 5. As can be seen from FIG. 5 the conversion of propylene at the end of the test was equal to about 30% after 300 hours of continuous running without any modification of the above reaction conditions.

It is clear that the performances of the catalyst can be perfectly compared, with respect to the life and consequently productivity of the catalyst, with those obtained using the material prepared according to example 1.

Example 9

An alkylation test of benzene with ethylene is carried out in a stirred batch reactor, charging the catalyst, the aromatic and subsequently—when the following temperature conditions have been reached—the quantity of ethylene necessary for obtaining the molar ratio between the reagents specified below.

Temp.=180° C.

Pressure=45 bar

Benzene charged=400 cc

[C6]/[C2]=4.4

Catalyst=1.7 g

During the test samples of the reaction liquid are taken in such quantities as not to greatly modify the total reaction volume and analyzed by gas-chromatography with a Perkin-Elmer instrument, PTV injector on column, temperature programmed from 80° to 240° C., wide-bore methylsilicon capillary column and FID detector. The catalyst used is that prepared according to example 1 (CATALYST A).

Figure 6:
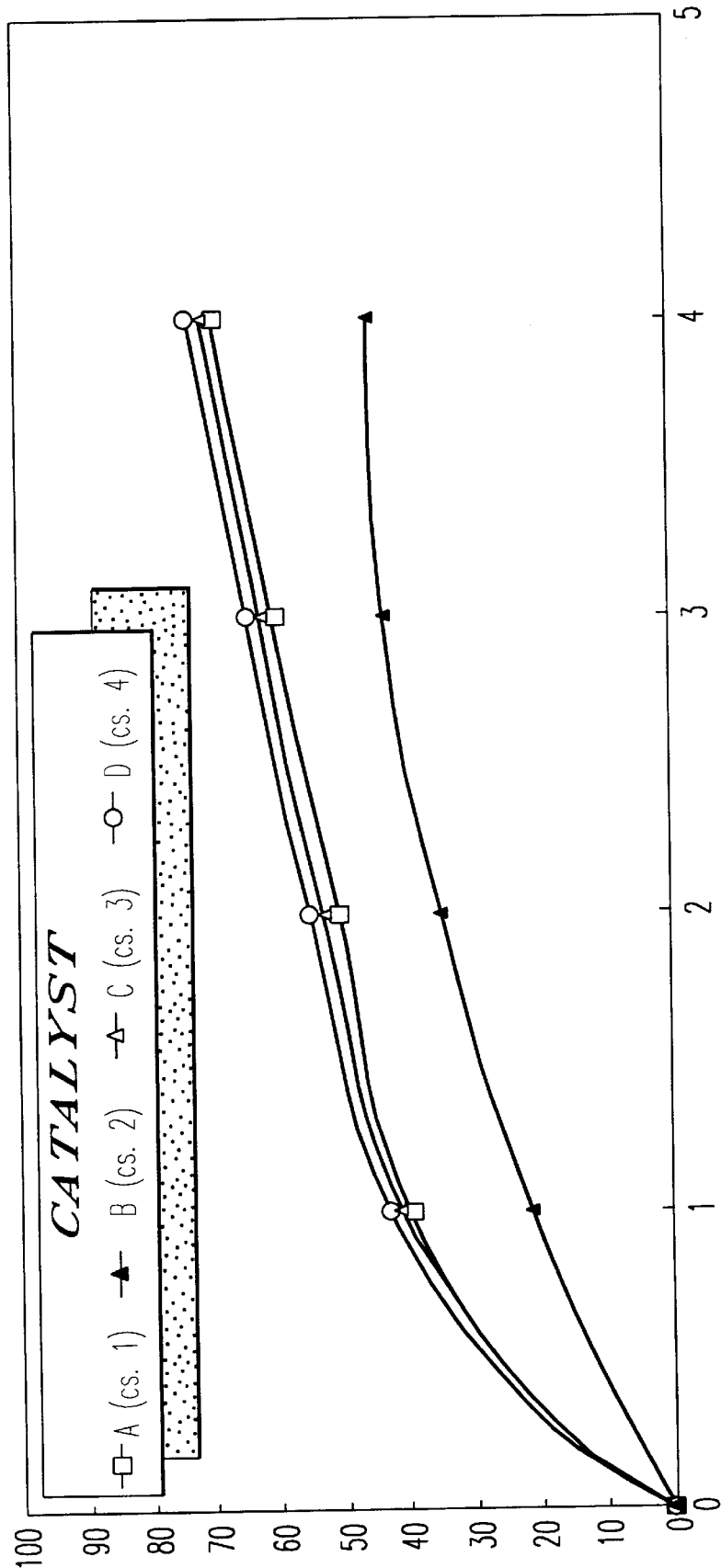
FIG. 6 is a graph showing the conversion trend of ethylene in relation to the time on stream for each of Catalysts A–D, in Examples 9–12, respectively.

FIG. 6 shows the conversion trend of the ethylene in the ordinate (%) in relation to the time on stream in hours (hr) in the abscissa using a stirred batch reactor.

Example 10—Comparative

A test is carried out under the conditions described in example 9 but using the catalyst prepared as described in example 2 (CATALYST B).

The conversion trend of the ethylene in relation to the reaction time is shown in FIG. 6.

From the inclination of the curve a lower reaction rate can be observed with respect to the previous example and a curve trend which indicates a deactivation of the catalyst with a reaction rate close to zero without a quantitative conversion of the ethylene.

Example 11

A test is carried out under the conditions described in example 9 but using the catalyst prepared as described in example 3 (CATALYST C).

The conversion trend of the ethylene in relation to the reaction time is shown in FIG. 6.

The behaviour of the catalyst is basically similar to that of the material of example 1.

Example 12

A test is carried out under the conditions described in example 9 but using the catalyst prepared as described in example 4 (CATALYST D).

The conversion trend of the ethylene in relation to the reaction time is shown in FIG. 6.

The behaviour of the catalyst is basically similar to that of the material of example 1.

TABLE I

CATALYST A

EXTRUSION PARAMETERS

| | |
|---|---|
| Binder content | 50 wt % |
| Acid added | acetic |
| Acid added/binder | 0.034 wt/wt |
| Extrusion pressure | 40–50 bar |
| Pellet: diameter/height | 2 mm/10 mm |

CATALYST

| | |
|---|---|
| SSA (BET 3 par.) | 460 m$^2$/g (506 m$^2$/g DR*) |
| "C" parameter (BET 3 par) | 1.977 |
| "N" parameter (BET 3 par) | 2.6 |
| Total pore volume | 0.52 cc/g |
| Macropore volume [A] | 0.01 cc/g |
| Mesopore volume [B] | 0.39 cc/g |
| Pore vol. with radius >100A [C] | 0.25 cc/g |
| \|[C]/([A] + [B])\| | 62% |
| Micropore volume | 0.12 cc/g |
| Crushing strength along diameter | 31 Kg |

TABLE II

CATALYST B

EXTRUSION PARAMETERS

| | |
|---|---|
| Binder content | 50 wt % |
| Acid added | acetic |
| Acid added/binder | 0.049 wt/wt |
| Extrusion pressure | 220–240 bar |
| Pellet: diameter/height | 2 mm/10 mm |

CATALYST

| | |
|---|---|
| SSA (BET 3 par.) | 433 m$^2$/g (476 m$^2$/g DR*) |
| "C" parameter (BET 3 par) | 2.181 |
| "N" parameter (BET 3 par) | 2.7 |
| Total pore volume | 0.43 cc/g |
| Macropore volume [A] | 0.00 cc/g |
| Mesopore volume [B] | 0.31 cc/g |
| Pore vol. with radius >100A [C] | 0.07 cc/g |
| \|[C]/([A] + [B])\| | 23% |
| Micropore volume | 0.12 cc/g |
| Crushing strength along diameter | 34 Kg |

TABLE III

CATALYST C

EXTRUSION PARAMETERS

| | |
|---|---|
| Binder content | 50 wt % |
| Acid added | acetic |
| Acid added/binder | 0.038 wt/wt |
| Extrusion pressure | 4–6 bar |
| Pellet: diameter/height | 2 mm/10 mm |

CATALYST

| | |
|---|---|
| SSA (BET 3 par.) | 458 m$^2$/g (492 m$^2$/g DR*) |
| "C" parameter (BET 3 par) | 1.960 |
| "N" parameter (BET 3 par) | 2.5 |
| Total pore volume | 0.81 cc/g |
| Macropore volume [A] | 0.14 cc/g |
| Mesopore volume [B] | 0.55 cc/g |
| Pore vol. with radius >100A [C] | 0.40 cc/g |
| {[C]/([A] + [B])} | 58% |
| Micropore volume | 0.12 cc/g |
| Crushing strength along diameter | 7 Kg |

TABLE IV

CATALYST D

EXTRUSION PARAMETERS

| | |
|---|---|
| Binder content | 50 wt % |
| Acid added | acetic |
| Acid added/binder | 0.047 wt/wt |
| Extrusion pressure | 20–30 bar |
| Pellet: diameter/height | 2 mm/10 mm |

CATALYST

| | |
|---|---|
| SSA (BET 3 par.) | 506 m$^2$/g (556 m$^2$/g DR*) |
| "C" parameter (BET 3 par) | 1.187 |
| "N" parameter (BET 3 par) | 2.7 |
| Total pore volume | 0.84 cc/g |
| Macropore volume [A] | 0.28 cc/g |
| Mesopore volume [B] | 0.44 cc/g |
| Pore vol. with radius >100A [C] | 0.51 cc/g |
| \|[C]/([A] + [B])\| | 71% |
| Micropore volume | 0.12 cc/g |
| Crushing strength along diameter | 19 Kg |

TABLE V

CATALYST A (after alkylation test)

CATALYST

| | |
|---|---|
| SSA (BET 3 par.) | 242 m$^2$/g (248 m$^2$/g DR*) |
| "C" parameter (BET 3 par) | 135 |
| "N" parameter (BET 3 par) | 5.6 |
| Total pore volume | 0.40 cc/g |
| Macropore volume [A] | 0.01 cc/g |
| Mesopore volume [B] | 0.34 cc/g |
| Micropore volume | 0.05 cc/g |

TABLE VI

CATALYST B (after alkylation test)

CATALYST

| | |
|---|---|
| SSA (BET 3 par.) | 287 m$^2$/g (316 m$^2$/g DR*) |
| "C" parameter (BET 3 par) | 489 |
| "N" parameter (BET 3 par) | 3.9 |
| Total pore volume | 0.37 cc/g |
| Macropore volume [A] | 0.00 cc/g |
| Mesopore volume [B] | 0.27 cc/g |
| Micropore volume | 0.10 cc/g |

DR* = Dubinin Radushkevich Method

Example 13

A transalkylation test of benzene is carried out with a mixture, whose composition is indicated in the following table, which simulates a typical composition of "cumene bottoms".

TABLE VII

| "Cumene bottoms" | % (w/w) | Reaction condition |
|---|---|---|
| Cumene | 5.2 | temp. = 200° C. |
| N-propylbenzene | 130 ppm | Press. = 30 bar |
| Phenyl-C4 | 0.5 | benzene = 250 g |
| Phenyl-C5 | 0.8 | Cumene bottoms = 90 g |
| m,o,p diisopropylbz | 73.6 | Catalalyst = 3.5 g |
| Heavies | 19.8 | |

The catalyst is that prepared according to example 1 (CATALYST A) and is placed inside appropriate rotating baskets with a rotation rate equal to 800 rpm. The transalkylation test is carried out by charging into a stirred autoclave, the catalyst, the benzene and subsequently, when the temperature conditions indicated in table VII above have been reached, the mixture of "cumene bottoms".

Figure 7:
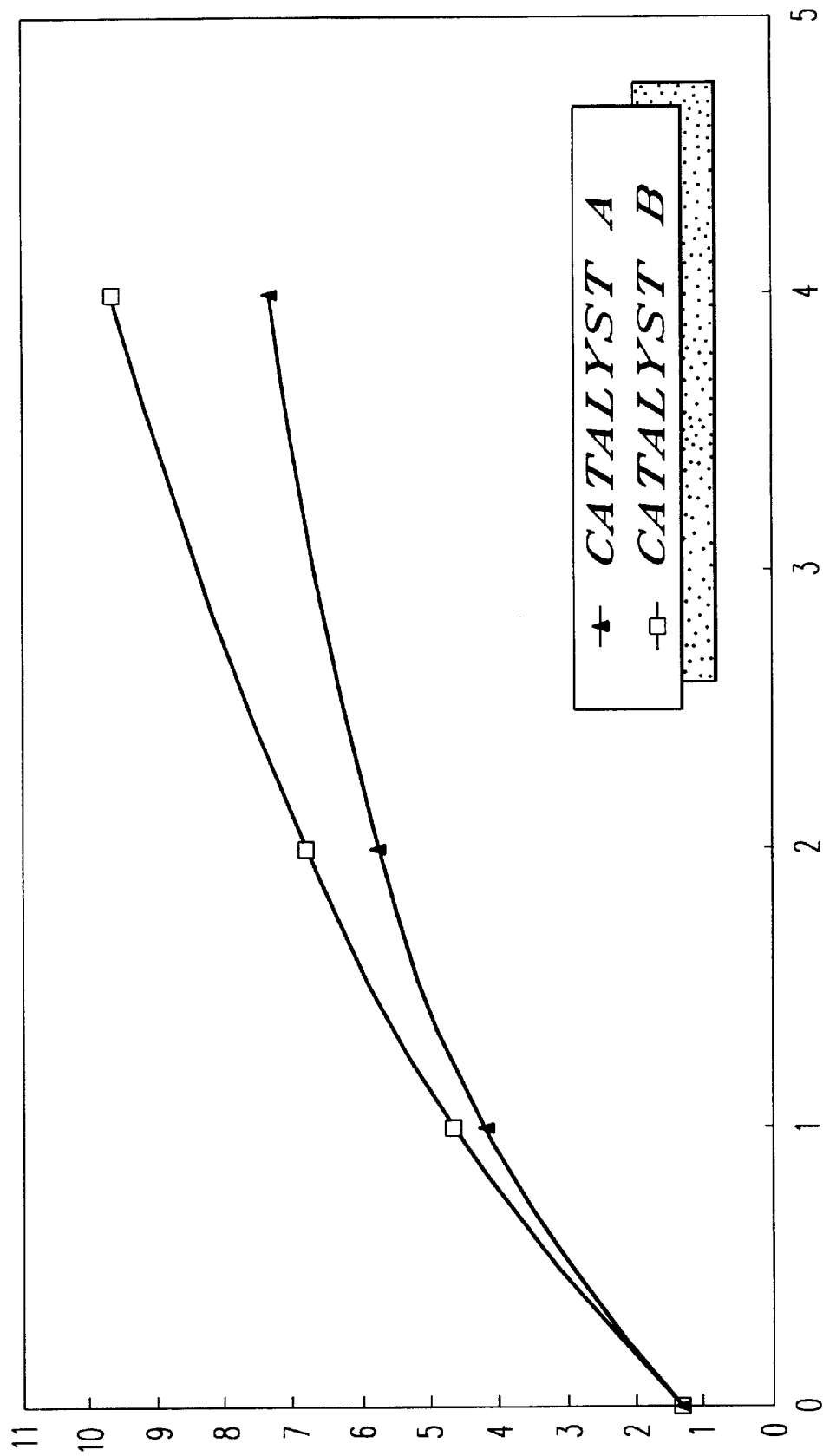
FIG. 7 is a graph showing the trend of the concentration of cumene in relation to reaction time for Catalysts A and B in Examples 13 and 14, respectively.

FIG. 7 shows the trend of the concentration of cumene (%) in the ordinates in relation to the reaction time expressed in hours, in the abscissa (CATALYST A CURVE). The analysis of the liquid sample is carried out using the equipment and conditions described in example 9.

Example 14—Comparative

A test is carried out under the same conditions described in example 13 but using the catalyst prepared as described in example 2 (CATALYST B).

The trend of the concentration of Cumene in relation to the reaction time is shown in FIG. 7 (CATALYST B CURVE).

From the gradient of the curve a lower reaction rate can be observed with respect to the curve obtained in example 13 together with a tendency to reach a plateau which indicates a more rapid deactivation of the catalyst.

We claim:

1. Catalytic composition comprising zeolite Beta or modified zeolite Beta, and an inorganic binder selected from the group consisting of aluminum oxide, magnesium oxide, natural clays, and mixtures thereof, wherein at least 25% of the pore volume obtained by adding the fractions of mesoporosity and macroporosity present in the catalytic composition itself consists of pores with a radius higher than 100 Å, and wherein the porosity in the fraction with a radius which is greater than 450 Å is less than 0.25 cc/g when the diameter of the catalytic particles is less than or equal to 0.8 mm.

2. Catalytic composition according to claim 1 wherein the porosity obtained by adding the fractions of mesoporosity and macroporosity present in the catalytic composition itself, is at least 35% of pore volume with a radius higher than 100 Å.

3. Catalytic composition according to claim 1 wherein the binder comprises alumina.

4. Process for the alkylation of aromatic compounds comprising putting said compounds in contact with a light olefin in the presence of a catalytic composition in accordance with any one of claims 1 or 2, operating at a temperature of between 100° and 300° C. and a pressure of between 10 and 50 atm and a WHSV space velocity of between 0.1 and 200 $h^{-1}$.

5. Process according to claim 4 wherein the temperature is between 120° and 230° C., the pressure between 20 and 45 atm and the WHSV space velocity between 1 and 10 $h^{-1}$.

6. Process according to claim 4 wherein the molar ratio between aromatic compound and olefin is between 1 and 20.

7. Process according to claim 4 wherein the molar ratio between aromatic compound and olefin is between 2 and 8.

8. Process for the transalkylation of an aromatic hydrocarbon which comprises putting the aromatic hydrocarbon in contact with a polyalkylated aromatic hydrocarbon under at least partial liquid phase conditions in the presence of a catalytic composition according to any one of claims 1 or 2.

9. Process according to claim 8 carried out at a temperature of between 100° and 350° C., at a pressure of between 10 and 50 atms and at a WHSV of between 0.1 and 200 $hours^{-1}$.

10. Process in accordance with claim 9 carried out at a temperature of between 150° and 300° C., at a pressure of between 20 and 45 atms and at a WHSV of between 0.1 and 10 $hours^{-1}$.

11. Process according to claim 8 wherein the molar ratio betwen the aromatic hydrocarbon and polyalkylated aromatic hydrocarbon is between 1 and 30.

12. Process according to claim 8 wherein the aromatic hydrocarbon is selected from benzene, toluene, ethylbenzene and xylene.

13. Process according to claim 12 wherein the aromatic hydrocarbon is benzene.

14. Process according to claim 8 wherein the polyalkylated aromatic hydrocarbon is selected from diethylbenzene and diisopropylbenzene.

15. Process according to claim 8 wherein the aromatic hydrocarbon is benzene and the polyalkylated aromatic hydrocarbon is diethylbenzene.

16. Process according to claim 8 wherein the aromatic hydrocarbon is benzene and the polyalkylated aromatic hydrocarbon is diisopropylbenzene.

* * * * *

UNITED STATES PATENT AND TRADEMARK OFFICE
CERTIFICATE OF CORRECTION

PATENT NO. : 5,811,612
DATED : September 22, 1998
INVENTOR(S): Gianni GIROTTI, et al.

It is certified that error appears in the above-identified patent and that said Letters Patent is hereby corrected as shown below:

On the title page, Item [30], the Foreign Application Priority Data, is incorrect. It should read:

--Jun. 16, 1994   [IT]   Italy.............MI94A1252--

Signed and Sealed this

Twenty-fourth Day of August, 1999

Attest:

Q. TODD DICKINSON

*Attesting Officer*      *Acting Commissioner of Patents and Trademarks*

UNITED STATES PATENT AND TRADEMARK OFFICE
CERTIFICATE OF CORRECTION

PATENT NO. :      5,811,612
DATED:       :      September 22, 1998
INVENTOR(S) :      Girotti et al.

It is certified that error appears in the above-identified patent and that said Letters patent is hereby corrected as shown below:

Column 4,    line 22, delete "A" and insert --Å--.

Signed and Sealed this

Twenty-fourth Day of October, 2000

Attest:

Q. TODD DICKINSON

*Attesting Officer*        *Director of Patents and Trademarks*